United States Patent
Woloszko et al.

(10) Patent No.: US 9,456,865 B2
(45) Date of Patent: Oct. 4, 2016

(54) SYMMETRIC SWITCHING ELECTRODE METHOD AND RELATED SYSTEM

(71) Applicant: ArthroCare Corporation, Austin, TX (US)

(72) Inventors: Jean Woloszko, Austin, TX (US); Johnson E. Goode, III, Austin, TX (US); Philip M. Tetzlaff, Austin, TX (US)

(73) Assignee: ArthroCare Corporation, Austin, TX (US)

(*) Notice: Subject to any disclaimer, the term of this patent is extended or adjusted under 35 U.S.C. 154(b) by 0 days.

(21) Appl. No.: 14/621,610

(22) Filed: Feb. 13, 2015

(65) Prior Publication Data

US 2015/0164579 A1    Jun. 18, 2015

Related U.S. Application Data

(62) Division of application No. 12/785,563, filed on May 24, 2010, now Pat. No. 8,979,838.

(51) Int. Cl.
*A61B 18/14* (2006.01)
*A61B 18/04* (2006.01)
*A61B 18/12* (2006.01)
*A61B 18/00* (2006.01)

(52) U.S. Cl.
CPC ........... *A61B 18/148* (2013.01); *A61B 18/042* (2013.01); *A61B 18/1206* (2013.01); *A61B 18/14* (2013.01); *A61B 2018/0044* (2013.01); *A61B 2018/00178* (2013.01); *A61B 2018/124* (2013.01); *A61B 2018/144* (2013.01); *A61B 2018/1472* (2013.01)

(58) Field of Classification Search
CPC .......... A61B 2018/00625; A61B 2018/00178; A61B 2018/1472; A61B 2018/00583; A61B 2018/00708; A61B 2018/122; A61B 2018/1226; A61B 2018/124; A61B 2018/1412; A61B 18/042; A61B 18/148
USPC ............. 606/39, 41, 48, 50; 607/98, 99
See application file for complete search history.

(56) References Cited

U.S. PATENT DOCUMENTS

| | | | | |
|---|---|---|---|---|
| 6,056,747 A * | 5/2000 | Saadat | ............. | A61B 18/14 606/42 |
| 7,611,509 B2 * | 11/2009 | Van Wyk | ............. | A61B 18/1485 606/37 |
| 7,727,232 B1 * | 6/2010 | Maurer | ............. | A61B 18/1402 606/48 |
| 2008/0015565 A1 * | 1/2008 | Davison | ............. | A61B 18/1206 606/37 |

* cited by examiner

*Primary Examiner* — Michael Peffley
*Assistant Examiner* — Thomas Giuliani
(74) *Attorney, Agent, or Firm* — David A. Warmbold

(57) ABSTRACT

Electrosurgical system and related methods that include: producing energy by a generator of an electrosurgical controller, the generator comprises a first terminal coupled to a first electrode of an electrosurgical wand, and the generator comprises a second terminal coupled to a second electrode of the electrosurgical wand; forming, responsive to the energy, a plasma proximate to the first electrode, and acting as a current return by the second electrode; reducing energy output of the generator such that the plasma proximate the first electrode is extinguished, the reducing energy output during periods of time when the electrosurgical controller is commanded to produce energy; producing energy from the generator with the first terminal coupled to the first electrode and the second terminal coupled to the second electrode; and forming, responsive to the energy, a plasma proximate to the second electrode, and acting as a current return by the first electrode.

12 Claims, 9 Drawing Sheets

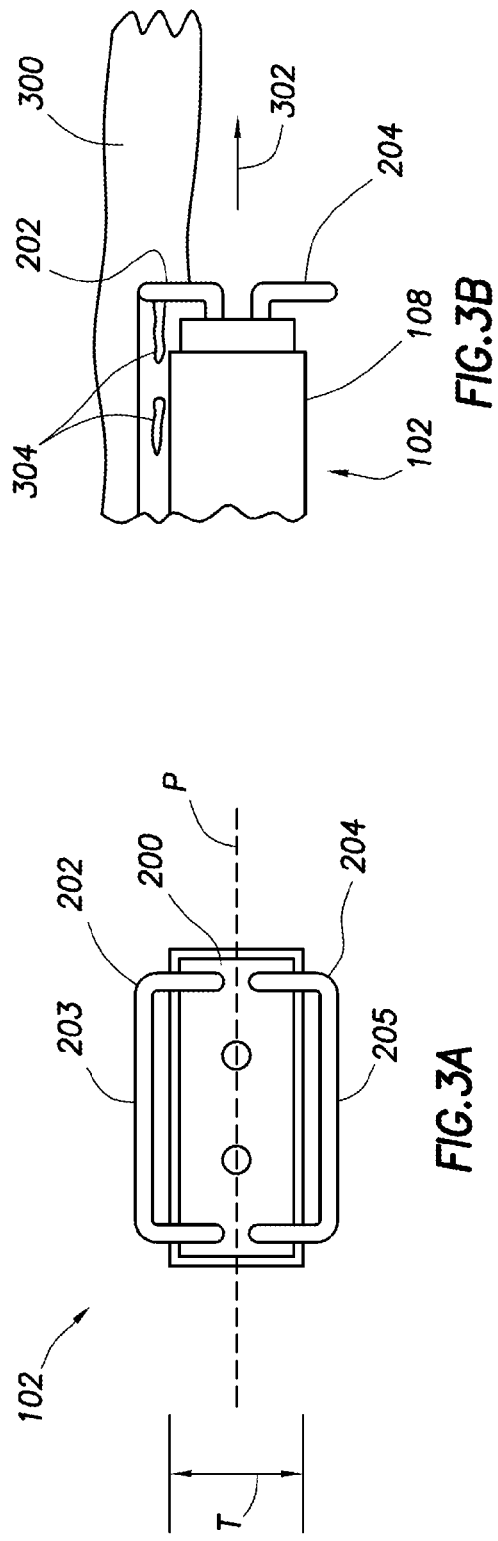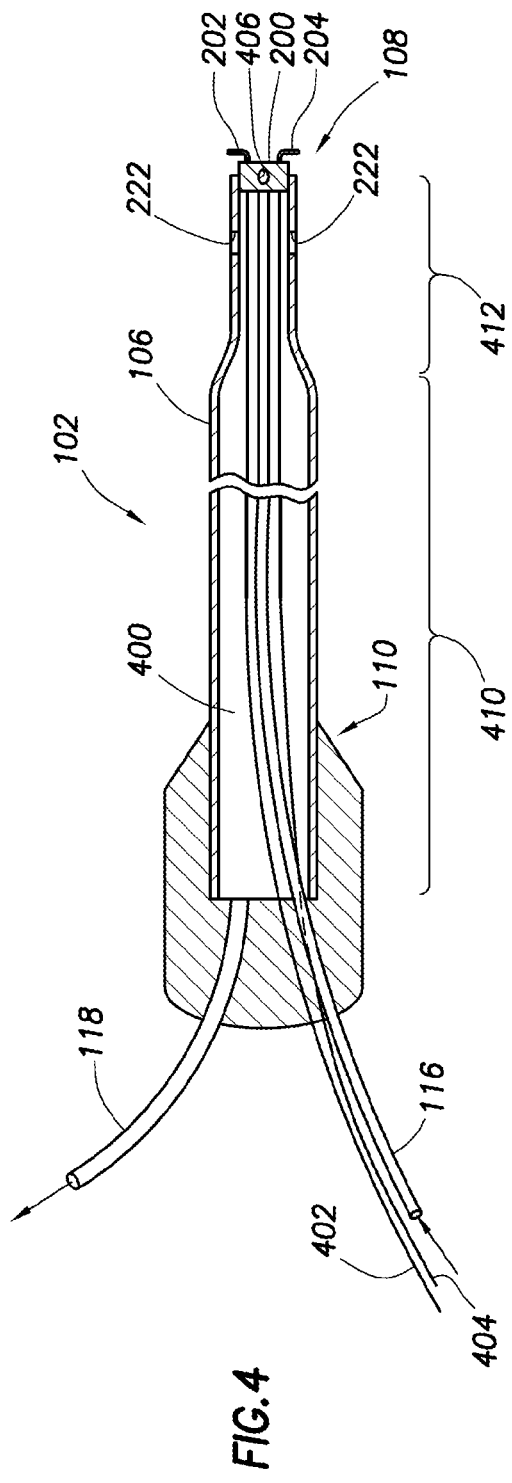

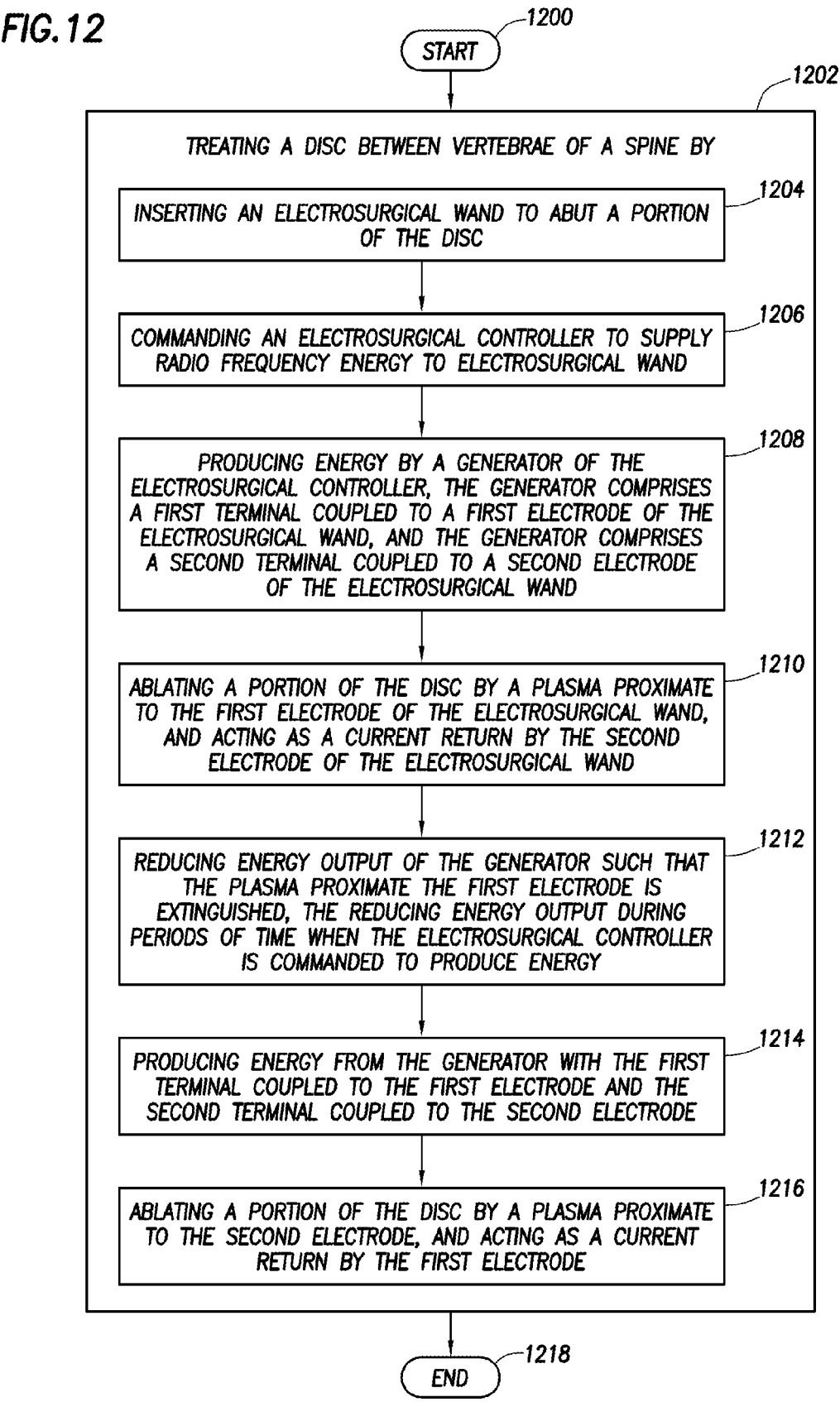

SYMMETRIC SWITCHING ELECTRODE METHOD AND RELATED SYSTEM

CROSS-REFERENCE TO RELATED APPLICATIONS

This application is a divisional of U.S. Pat. No. 8,979,838 filed May 24, 2010. The entire text of the above-referenced disclosure is specifically incorporated herein by reference without disclaimer.

BACKGROUND

Electrosurgical systems are used by physicians to perform specific functions during surgical procedures. For example, electrosurgical systems use high frequency electrical energy to remove soft tissue such as sinus tissue, adipose tissue, meniscus, cartilage and/or sinovial tissue in a joint, or to remove portions of a disc between vertebrae (e.g., remove end-plate, remove annulus fibrosus).

However, the spacing between vertebrae not only limits the number and spacing of electrodes on the tip of an electrosurgical wand, but also limits the amount of movement possible with the electrosurgical wand during spinal procedures. For example, narrow spacing between the vertebrae in many cases does not allow a surgeon to turn the electrosurgical wand over with the wand tip within the disc between the vertebrae. Despite the physical limitations, both the portion of the disc near the adjacent upper vertebrae, and the portion of the disc near the adjacent lower vertebrae, may need to be treated. Having an electrosurgical wand with dedicated upper and lower active electrodes, along with a dedicated return electrode, may simultaneously treat both sides of the disc, but is impractical both because of space considerations and because having two active electrodes may cause excessive muscle and/or nerve stimulation. Having an electrosurgical wand a dedicated active electrode that only treats one side of the disc one side of the disc requires the surgeon to remove wand, turn the wand over, and re-insert the wand to treat the other side of the disc—a series of events required many times during a spinal procedure, rendering the procedure time consuming and impractical.

Any advance that makes the treatment of tissue in confined spaces faster and easier for the surgeon, and less traumatic for the patient, would provide a competitive advantage.

BRIEF DESCRIPTION OF THE DRAWINGS

For a detailed description of exemplary embodiments, reference will now be made to the accompanying drawings in which:

FIG. 3A shows an end elevation view of a wand in accordance with at least some embodiments;

FIG. 3B shows a side elevation view of a wand in accordance with at least some embodiments;

FIG. 4 shows a cross-sectional view of a wand in accordance with at least some embodiments;

FIG. 12 shows a method in accordance with at least some embodiments.

NOTATION AND NOMENCLATURE

Figure 1:
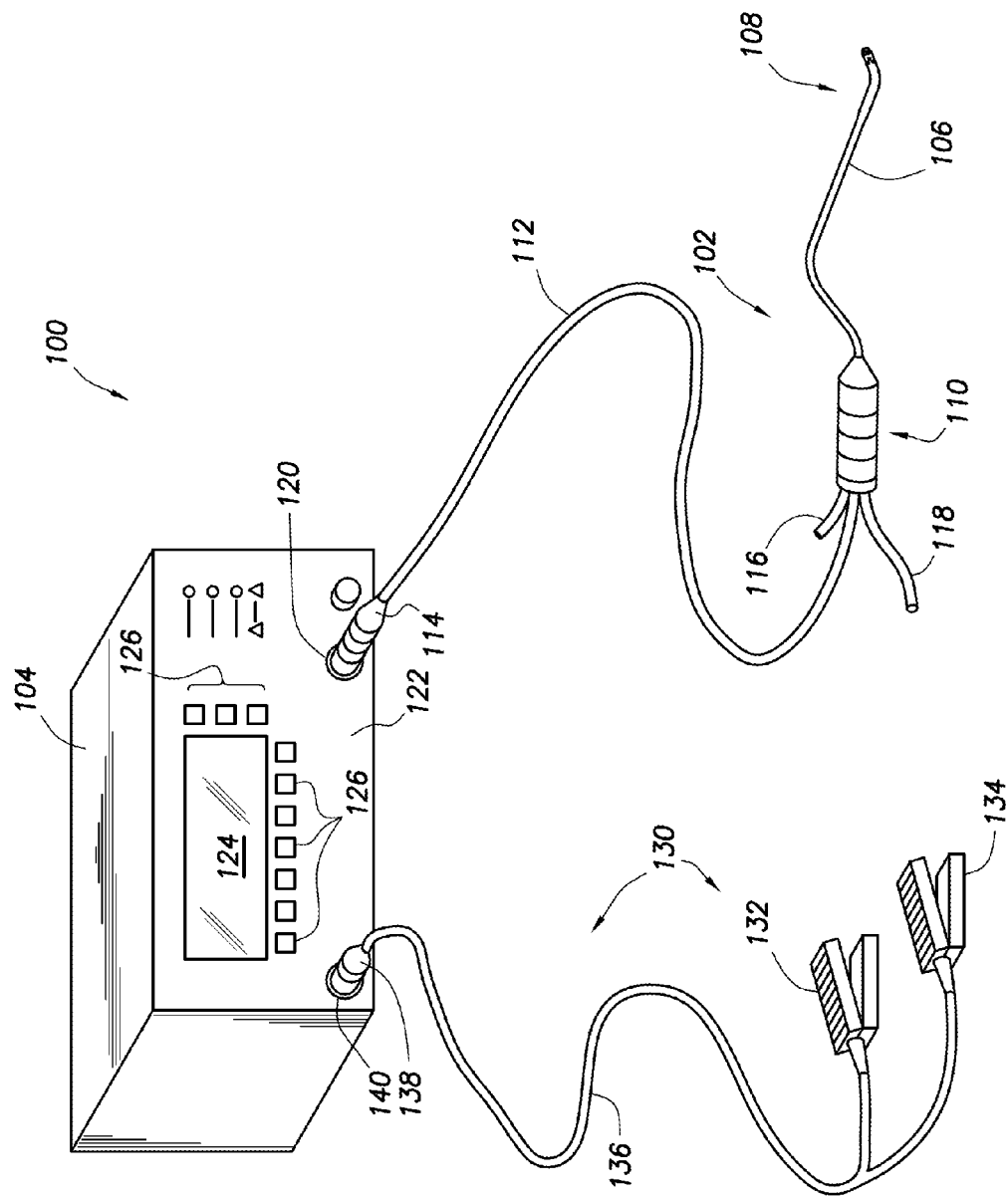
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrons with respect to an active electrode, and/or an electrode of an electrical surgical wand which does not itself produce an electrically-induced tissue-altering effect on tissue targeted for treatment.

"Substantially", in relation to exposed surface areas, shall mean that exposed surface areas as between two electrodes are same, or differ by no more than twenty five (25) percent.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). The wand 102 comprises an elongate shaft 106 that defines distal end 108 where at least some electrodes are disposed. The elongate shaft 106 further defines a handle or proximal end 110, where a physician grips the wand 102 during surgical procedures. The wand 102 further comprises a flexible multi-conductor cable 112 housing a plurality of electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116 and a second flexible tubular member 118. In some embodiments, the flexible tubular member 116 is used to provide saline to the distal end 108 of the wand. Likewise in some embodiments, flexible tubular member 118 is used to provide aspiration to the distal end 108 of the wand.

Still referring to FIG. 1, a display device or interface panel 124 is visible through the outer surface 122 of the controller 104, and in some embodiments a user may select operational modes of the controller 104 by way of the interface device 124 and related buttons 126.

In some embodiments the electrosurgical system 100 also comprises a foot pedal assembly 130. The foot pedal assembly 130 may comprise one or more pedal devices 132 and 134, a flexible multi-conductor cable 136 and a pedal connector 138. While only two pedal devices 132, 134 are shown, one or more pedal devices may be implemented. The outer surface 122 of the controller 104 may comprise a corresponding connector 140 that couples to the pedal connector 138. A physician may use the foot pedal assembly 130 to control various aspects of the controller 104, such as the operational mode. For example, a pedal device, such as pedal device 132, may be used for on-off control of the application of radio frequency (RF) energy to the wand 102, and more specifically for control of energy in an ablation mode. A second pedal device, such as pedal device 134, may be used to control and/or set the operational mode of the electrosurgical system. For example, actuation of pedal device 134 may switch between energy levels of an ablation mode.

The electrosurgical system 100 of the various embodiments may have a variety of operational modes. One such mode employs Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments, such as surgical procedures on a disc between vertebrae, the electrically conductive fluid is delivered in the vicinity of the active electrode and/or to the target site by the wand 102, such as by way of the internal passage and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 100 of FIG. 1 may also in particular situations be useful for sealing larger arterial vessels (e.g., on the order of about 1 mm in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation® technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes).

A more complete description of the various phenomena can be found in commonly assigned U.S. Pat. Nos. 6,355,032; 6,149,120 and 6,296,136, the complete disclosures of which are incorporated herein by reference.

Figure 2:
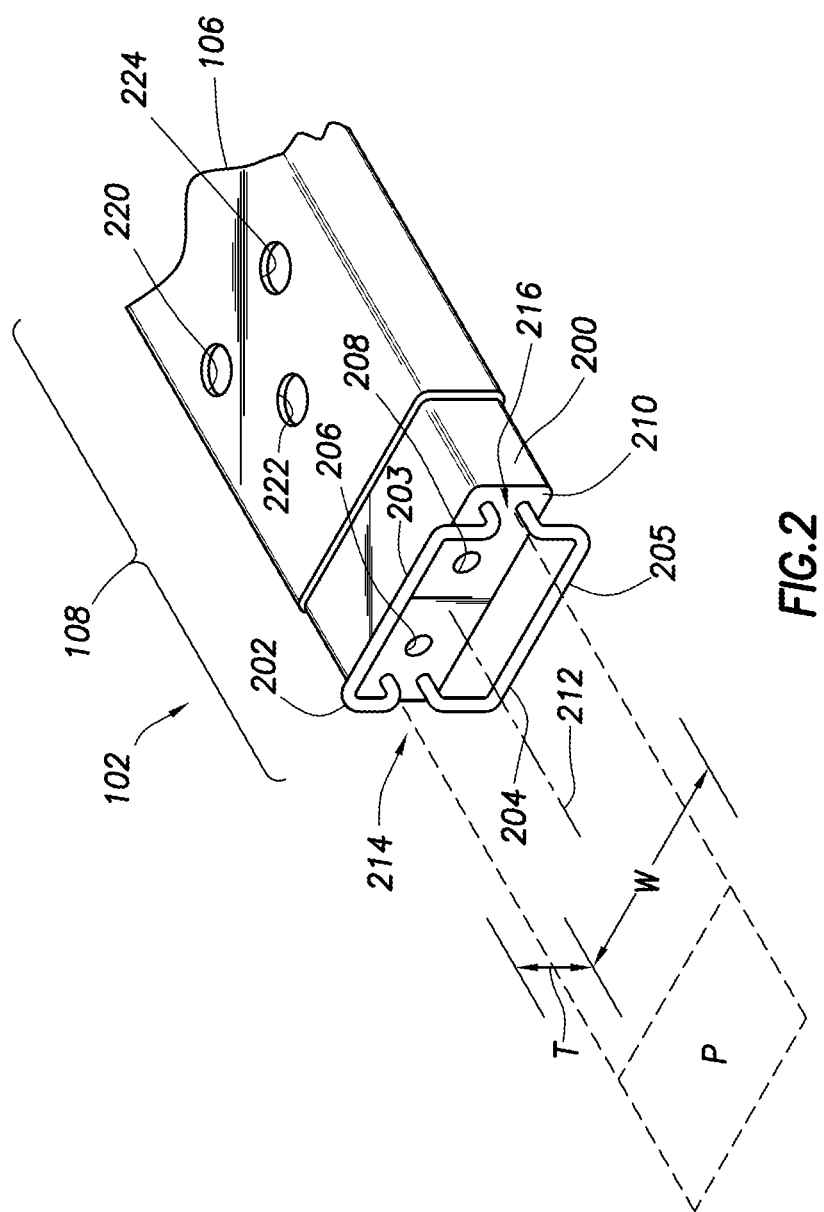
FIG. 2 shows a perspective view a portion of a wand in accordance with at least some embodiments.

FIG. 2 illustrates a perspective view of the distal end 108 of wand 102 in accordance with at least some embodiments.

In particular, the distal end 108 defines a width (labeled W in the figure) and a thickness (labeled T in the figure). In some embodiments the elongate shaft 106 is made of a metallic material (e.g., Grade TP304 stainless steel hypodermic tubing). In other embodiments, the elongate shaft may be constructed of other suitable materials, such as inorganic insulating materials. For reasons that will become clear below, in at least some embodiments the metallic material of the elongate shaft 106 is not electrically grounded or electrically coupled to the generator of the controller 104. The elongate shaft 106 may define a circular cross-section at the handle or proximal end 110 (not shown in FIG. 2), and the distal end 108 may be flattened to define rectangular cross-section. In other embodiments, the flattened portion may define a semi-circular cross-section. For wands intended for use in spinal procedures, the width W may be a centimeter or less, and in some cases 5 millimeters. Likewise, for wands intended use in spinal procedures, the thickness T may be 4 millimeters or less, and in some cases 3 millimeters. Other dimensions, particularly larger dimensions, may be equivalently used when the surgical procedure allows.

In embodiments where the elongate shaft is metallic, the distal end 108 may further comprise a non-conductive spacer 200 coupled to the elongate shaft 106. In some cases the spacer 200 is ceramic, but other non-conductive materials resistant to degradation when exposed to plasma may be equivalently used (e.g., glass). The spacer 200 supports electrodes of conductive material, with illustrative electrodes labeled 202 and 204 in FIG. 2. In accordance with at least some embodiments, the upper electrode 202 is disposed above a plane that bisects the thickness (a portion of an illustrative plane that bisects the thickness labeled P in FIG. 2), and with the lower electrode 204 disposed below the plane that bisects the thickness.

Each electrode 202 and 204 defines an exposed surface area of conductive material, and in accordance with at least some embodiments the exposed surface area as between the upper electrode 202 and the lower electrode 204 is substantially the same. In the particular embodiment of FIG. 2, each electrode 202 and 204 is a loop of wire of particular diameter. The wire diameter selected for a particular wand depends, at least in part, on the parasitic stimulation of muscle and/or nerves that can be tolerated by the particular medical procedure. Greater parasitic stimulation is present with greater exposed surface areas of the conductors (i.e., greater wire diameters and length), and less parasitic stimulation is present with less exposed surface area (i.e., smaller wire diameters and lengths). However, as wire diameters decrease, the wires become more fragile and subject to bending or breaking. For embodiments using loops of wire such as in FIG. 2, the wire diameter may be between and including 0.008 inches to 0.015 inches. In a particular embodiment for removal of intervertebral disc material (e.g., for discectomy procedures in order to perform interbody vertebral fusion), the loops of wire may be tungsten having a diameter of 0.012 inches and have an exposed length of approximately 0.228 inches.

In accordance with at least some embodiments, not only do the electrodes define substantially the same exposed surface area as between the upper and lower electrodes, but also the shape as between the upper and lower electrodes is symmetric. In particular, the upper electrode 202 defines a particular shape, and likewise the lower electrode defines a particular shape. The shapes defined by the electrodes 202 and 204 are symmetric about the plane P that bisects the thickness T. More particularly still, in some embodiments the electrodes 202 and 204 are mirror images of each other reflected about the plane P that bisects the thickness. In other embodiments, the shape of the electrodes may be non-symmetrical about the plane P, even if the exposed surface areas are substantially the same.

Still referring to FIG. 2, the illustrative wire loop electrodes 202 and 204 each define a straight portion 203 and 205, respectively. In at least some embodiments, each straight portion 203 and 205 are parallel to the plane P that bisects the thickness of the distal end 108. In embodiments where the electrodes are symmetric, the straight portions 203 and 205 are likewise parallel to each other. However, in other embodiments the straight portions 203 and 205 are each be parallel to the plane P, but not necessarily parallel to each other.

In some embodiments saline is delivered to the distal end 108 of wand, possibly to aid in plasma creation. Still referring to FIG. 2, FIG. 2 illustrates discharge apertures 206 and 208 on the distal end 108 between the electrodes 202 and 204. In the particular embodiment illustrated, two discharge apertures are shown, but one or more discharge apertures are contemplated. The discharge apertures 206 and 208 are fluidly coupled to the flexible tubular member 116 (FIG. 1) by way of a fluid conduit within the wand 102. Thus, saline or other fluid may be pumped into the flexible tubular member 116 (FIG. 1) and discharge through the discharge apertures 206 and 208. In some cases, the fluid may discharge straight out of each discharge aperture 206 and 208 (i.e., normal to the front surface 210 of the spacer 200), but in other cases the fluid may discharge at an angle. Consider that the distal end 108 of the wand 102 defines a wand tip axis 212. In a particular embodiment, each discharge aperture 206 and 208 is created and/or formed to direct discharging fluid out the aperture a non-zero angle relative to the wand tip axis 212. For example, the discharge aperture 206 may direct discharging fluid toward the bends 214 in the wire loop electrodes 202 and 204. Likewise, the discharge aperture 208 may direct discharging fluid toward the bends 216 in the wire loop electrodes 202 and 204. The inventors of the present specification have found that discharging the fluid from the apertures at a non-zero angle appears to aid plasma creation. The discharge apertures are relatively small, on the order of 1 millimeter or less. During spinal procedures, between and 10 and 60 milli-Liters (mL) per second (mL/s) total flows from the discharge apertures, and in particular cases 30 mL/s flows. Other flow volumes are contemplated for different procedures, with the amount of fluid flow through the apertures dependent upon the amount of fluid naturally present at the surgical site of the body.

In yet still further embodiments, aspiration is provided at the distal end 108 of the wand 102. FIG. 2 illustrates aspiration apertures 220, 222 and 224. While three such aspiration apertures are shown, one or more aspiration apertures are contemplated. Though not visible in the view of FIG. 2, in some case three or more additional aspiration apertures are present on the bottom side of the distal end 108. The aspiration apertures 220, 222 and 224 are disposed on the distal end 108, but as illustrated the aspiration apertures are closer to the proximal end 110 (FIG. 1) of the wand 102 than the discharge apertures 206 and 208. The aspiration apertures are fluidly coupled to flexible tubular member 118 (FIG. 1), possibly by way of a fluid conduit within the wand 102. In a particular embodiment, the flexible tubular member 118 resides within the handle of the proximal end 110 (FIG. 1) of the wand 102, but then seals to the elongate shaft 106 in such a way that the elongate shaft 106 itself becomes a portion of the fluid conduit for the aspiration apertures. The aspiration apertures 220, 222 and 224 aspirate the area near the distal end 108, such as to remove excess fluids and remnants of ablation. The aspiration apertures 220, 222 and 224 are disposed as close to the electrodes 202 and 204 as assembly considerations will allow, and in many cases 5 centimeters or less.

FIG. 3A illustrates an elevational end-view of the distal end 108 of the illustrative wand 102 in order to show further relationships of the electrodes 202 and 204. As discussed with respect to FIG. 2, the illustrative wire loop electrode 202 resides above a plane P that bisects the thickness T, and in the view of FIG. 3 plane P appears only as a line segment (shown in dashed form). Likewise, the illustrative wire loop electrode 204 resides below the plane P that bisects the thickness T. As discussed above, each of the illustrative wire loop electrodes 202 and 204 define a straight portion 203 and 205, respectively. FIG. 3 illustrates that, in at least some embodiments, the straight portion 203 of wire loop 202 resides above the plane P by more than half the thickness T. Likewise, the straight portion 205 of wire loop 204 resides below the plane P by more than half the thickness T. Stated otherwise, the physical relationship of the straight portions 203 and 205 to the balance of the distal end 108 is that each straight portion resides outside a boundary defined by the elongate shaft 106 and/or the spacer 200. Although not required in every case, the physical placement of the straight portions 203 and 205 relative to the elongate shaft 106 and/or the spacer 200 provides a useful feature in ablation in accordance with at least some embodiments.

Having the straight portions 203 and 205 residing outside a boundary defined by the elongate shaft 106 and/or spacer 200 provides an operational aspect where tissue to be removed is not removed by being fully ablated; rather, the physical relationship enables "slicing" of the tissue. FIG. 3B illustrates a side elevation view of the distal end 108 of the wand 102 in illustrative relation to tissue 300 to be removed. In particular, consider that plasma has been created near electrode 202. As the wand 102 moves in the direction illustrated by arrow 302, portions of the tissue 300 are "sliced" off the larger tissue portion 300. The "slicing" action itself may be by ablation of some of the tissue, but portions of the tissue are separated from the larger portion by the "slicing" action, as illustrated by portions 304. These portions 304 may be removed from the treatment area by the aspiration provided through aspiration ports (not visible in FIG. 3B). Although illustrative FIG. 3B shows the "slicing" action in only one direction, the "slicing" action may take place in the opposite direction as well. Moreover, while illustrative FIG. 3B shows the "slicing" action only with respect to electrode 202, the "slicing" action may likewise take place with respect to electrode 204.

FIG. 4 shows a cross-sectional elevation view of a wand 102 in accordance with at least some embodiments. In particular, FIG. 4 shows the handle or proximal end 110 coupled to the elongate shaft 106. As illustrated, the elongate shaft 106 telescopes within the handle, but other mechanisms to couple the elongate shaft to the handle may be equivalently used. The elongate shaft 106 defines internal conduit 400 that serves several purposes. For example, in the embodiments illustrated by FIG. 4 the electrical leads 402 and 404 extend through the internal conduit 400 to electrically couple to the electrodes 202 and 204, respectively. Likewise, the flexible tubular member 116 extends through the internal conduit 400 to fluidly couple to the apertures 206 and 208 (not visible in FIG. 4, but a fluid pathway 406 within the spacer 200 is visible).

The internal conduit 400 also serves as the aspiration route. In particular, FIG. 4 illustrates aspiration apertures 222 (one on top and another on bottom). In the embodiments illustrated, the flexible tubular member 118, through which aspiration is performed, couples through the handle and then fluidly couples to the internal conduit 400. Thus, the suction provided through flexible tubular member 118 provides aspiration at the aspiration apertures 222 (and others not visible). The fluids that are drawn into the internal fluid conduit 400 may abut the portion of the flexible tubular member 116 that resides within the internal conduit as the fluids are drawn along the conduit; however, the flexible tubular member 116 is sealed, and thus the aspirated fluids do not mix with the fluid (e.g., saline) being pumped through the flexible tubular member 116. Likewise, the fluids that are drawn into the internal fluid conduit 400 may abut portions of the electrical leads 402 and 404 within the internal fluid conduit 400 as the fluids are drawn along the conduit. However, the electrical leads are insulated with an insulating material that electrically and fluidly isolates the leads from any substance within the internal fluid conduit 400. Thus, the internal fluid conduit serves, in the embodiments shown, two purposes—one to be the pathway which the flexible tubular member 116 and electrical leads traverse to reach the distal end 108, and also as the conduit through which aspiration takes place. In other embodiments, the flexible tubular member 118 may extend partially or fully through the elongate shaft 106, and thus more directly couple to the aspiration apertures.

FIG. 4 also illustrates that, in accordance with at least some embodiments, a portion of the elongate shaft 106 is circular (e.g., portion 410) and another portion of the elongate shaft 106 is flattened (e.g., portion 412) to define a rectangular or semi-circular cross-section. In some embodiments, the distal 6 centimeters or less is flattened, and in some cases the last 4 centimeters. In other embodiments, the entire elongate shaft may define the rectangular or semi-circular cross-section. The offsets of the elongate shaft 106 are not visible in FIG. 4 because of the particular view; however, FIG. 5 shows illustrative offsets.

Figure 5:
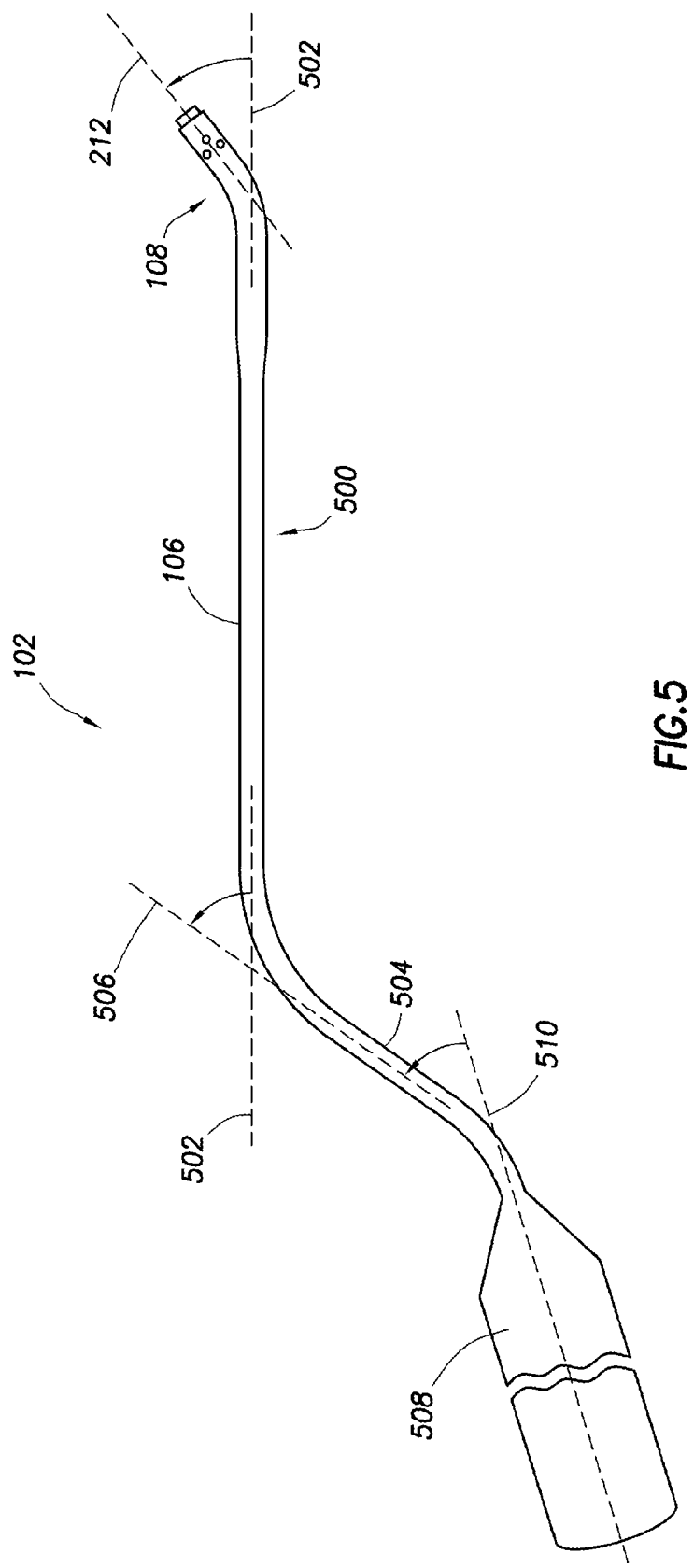
FIG. 5 shows an overhead view of a wand in accordance with at least some embodiments.

FIG. 5 shows an overhead view of the wand 102 in an orientation where the offsets in the elongate shaft 106 are visible. The illustrative wand 102 is designed and constructed for use in procedures where other equipment (e.g., an arthroscopic camera or surgical microscope) may be present and where those other devices prevent use of straight elongate shaft. In particular, the distal end 108 defines wand tip axis 212, and the elongate shaft 106 also defines a medial portion 500 which has an axis 502 (hereafter, the medial axis 502). In the particular embodiments illustrated the angle between the medial axis 502 and the wand tip axis 212 is non-zero, and in some embodiments the acute angle between the medial axis 502 and the wand tip axis is 35 degrees, but greater or lesser angles may be equivalently used.

Likewise, the elongate shaft 106 of FIG. 5 defines a proximal portion 504 with an axis 506 (hereafter, the proximal axis 506). In the particular embodiment illustrated the angle between the proximal axis 506 and the medial axis 502 is non-zero, and in some embodiments the acute angle between the proximal axis 506 and the medial axis 502 is 55 degrees, but greater or lesser angles may be equivalently used. Further still, the handle 508 of FIG. 5 defines an axis 510 (hereafter, the handle axis 510). In the particular embodiment illustrated the acute angle between the handle axis 510 and the proximal axis 506 is non-zero, and in some embodiments the acute angle between the handle axis 510 and the medial axis 506 is 40 degrees, but greater or lesser angles may be equivalently used.

Figure 6:
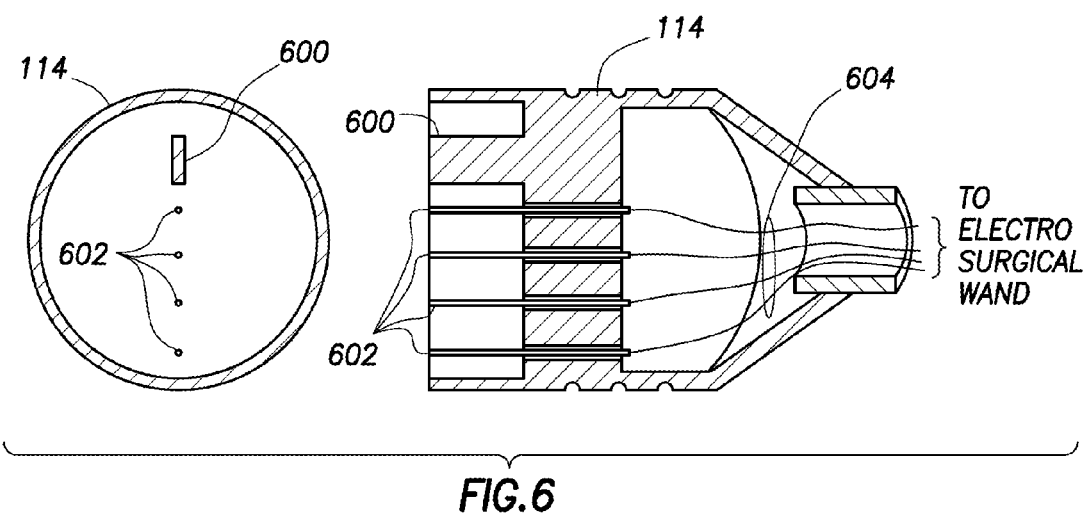
FIG. 6 shows both an elevational end-view (left) and a cross-sectional view (right) of a wand connector in accordance with at least some embodiments.

As illustrated in FIG. 1, flexible multi-conductor cable 112 (and more particularly its constituent electrical leads 402, 404 and possibly others) couple to the wand connector 114. Wand connector 114 couples the controller 104, and more particularly the controller connector 120. FIG. 6 shows both a cross-sectional view (right) and an end elevation view (left) of wand connector 114 in accordance with at least some embodiments. In particular, wand connector 114 comprises a tab 600. Tab 600 works in conjunction with a slot on controller connector 120 (shown in FIG. 7) to ensure that the wand connector 114 and controller connector 120 only couple in one relative orientation. The illustrative wand connector 114 further comprises a plurality of electrical pins 602 protruding from wand connector 114. In many cases, the electrical pins 602 are coupled one each to an electrical lead of electrical leads 604 (two of which may be leads 402 and 404 of FIG. 4). Stated otherwise, in particular embodiments each electrical pin 602 couples to a single electrical lead, and thus each illustrative electrical pin 602 couples to a single electrode of the wand 102. In other cases, a single electrical pin 602 couples to multiple electrodes on the electrosurgical wand 102. While FIG. 6 shows four illustrative electrical pins, in some embodiments as few as two electrical pins, and as many as 26 electrical pins, may be present in the wand connector 114.

Figure 7:
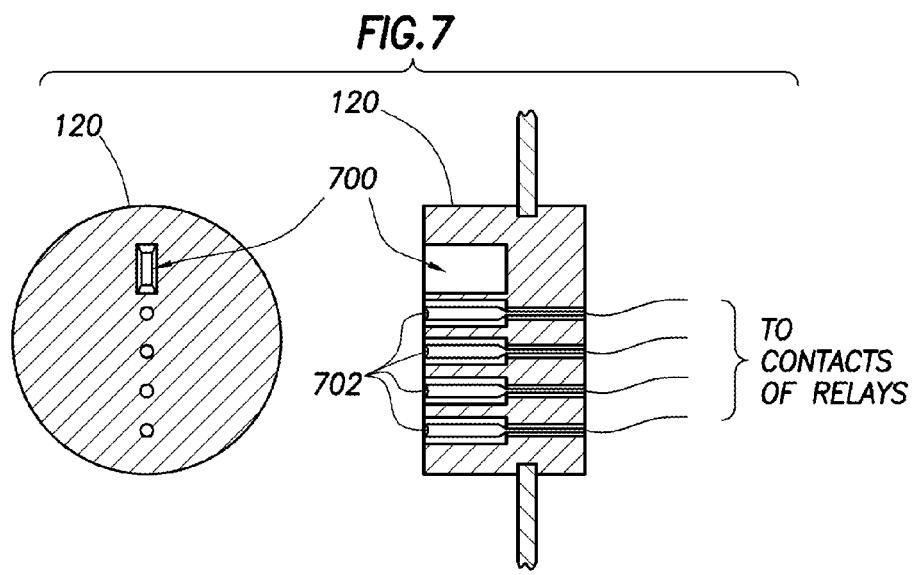
FIG. 7 shows both an elevational end-view (left) and a cross-sectional view (right) of a controller connector in accordance with at least some embodiments.

FIG. 7 shows both a cross-sectional view (right) and an end elevation view (left) of controller connector 120 in accordance with at least some embodiments. In particular, controller connector 120 comprises a slot 700. Slot 700 works in conjunction with a tab 600 on wand connector 114 (shown in FIG. 6) to ensure that the wand connector 114 and controller connector 120 only couple in one orientation. The illustrative controller connector 120 further comprises a plurality of electrical pins 702 residing within respective holes of controller connector 120. The electrical pins 702 are coupled to terminals of a voltage generator within the controller 104 (discussed more thoroughly below). When wand connector 114 and controller connector 120 are coupled, each electrical pin 702 couples to a single electrical pin 602. While FIG. 7 shows only four illustrative electrical pins, in some embodiments as few as two electrical pins, and as many as 26 electrical pins may be present in the wand connector 120.

While illustrative wand connector 114 is shown to have the tab 600 and male electrical pins 602, and controller connector 120 is shown to have the slot 700 and female electrical pins 702, in alternative embodiments the wand connector has the female electrical pins and slot, and the controller connector 120 has the tab and male electrical pins, or other combination. In other embodiments, the arrangement of the pins within the connectors may enable only a single orientation for connection of the connectors, and thus the tab and slot arrangement may be omitted. In yet still other embodiments, other mechanical arrangements to ensure the wand connector and controller connector couple in only one orientation may be equivalently used. In the case of a wand with only two electrodes, and which electrodes may be either active or return electrodes as the physical situation dictates, there may be no need to ensure the connectors couple in a particular orientation.

Figure 8:
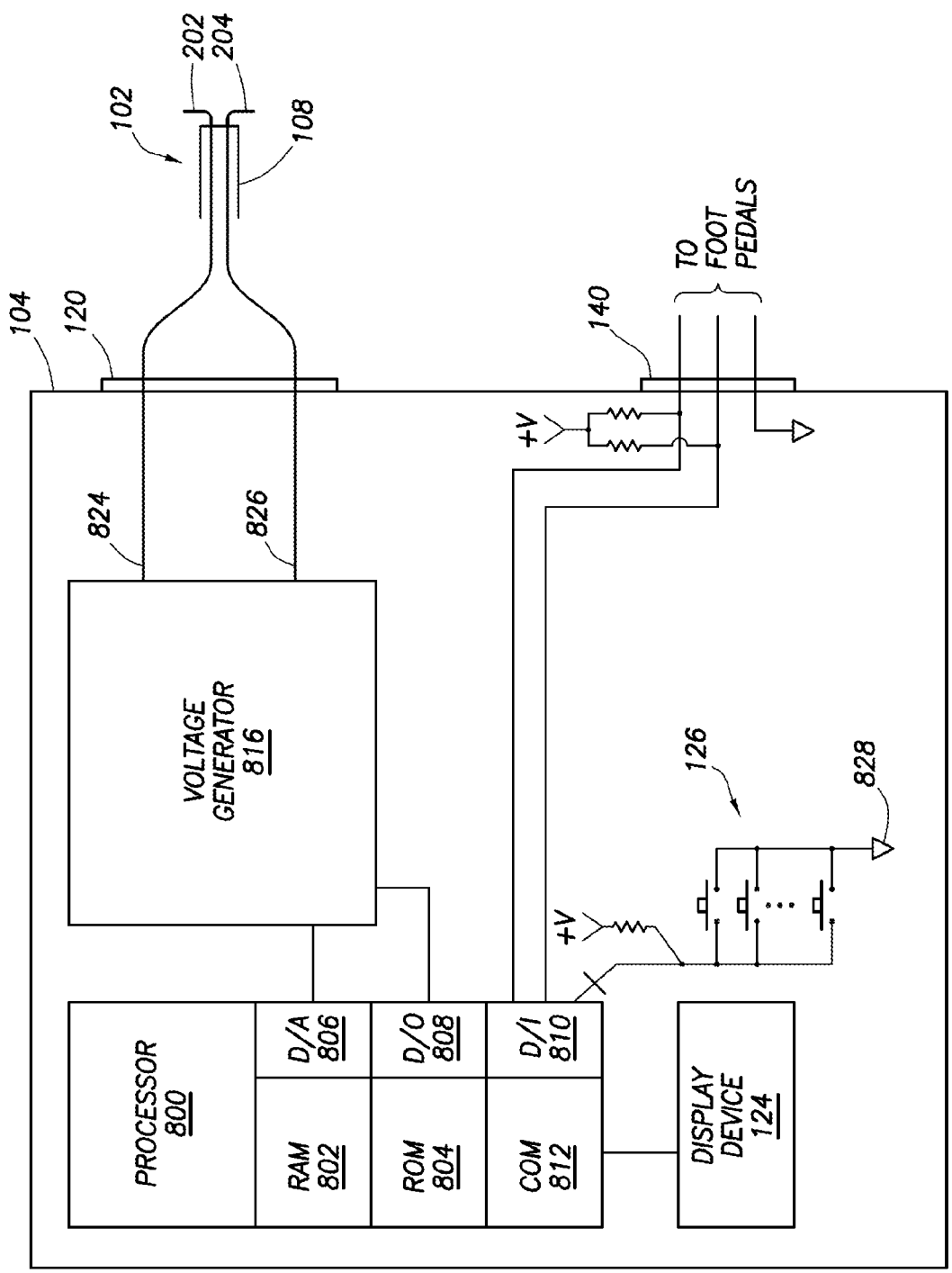
FIG. 8 shows an electrical block diagram of an electrosurgical controller in accordance with at least some embodiments.

FIG. 8 illustrates a controller 104 in accordance with at least some embodiments. In particular, the controller 104 comprises a processor 800. The processor 800 may be a microcontroller, and therefore the microcontroller may be integral with random access memory (RAM) 802, read-only memory (RAM) 804, digital-to-analog converter (D/A) 806, digital outputs (D/O) 808 and digital inputs (D/I) 810. The processor 800 may further provide one or more externally available peripheral busses, such as a serial bus (e.g., I²C), parallel bus, or other bus and corresponding communication mode. The processor 800 may further be integral with a communication logic 812 to enable the processor 800 to communicate with external devices, as well as internal devices, such as display device 124. Although in some embodiments the controller 104 may implement a microcontroller, in yet other embodiments the processor 800 may be implemented as a standalone central processing unit in combination with individual RAM, ROM, communication, D/A, D/O and D/I devices, as well as communication port hardware for communication to peripheral components.

ROM 804 stores instructions executable by the processor 800. In particular, the ROM 804 may comprise a software program that implements the various embodiments of periodically reducing voltage generator output to change position of the plasma relative to the electrodes of the wand (discussed more below), as well as interfacing with the user by way of the display device 124 and/or the foot pedal assembly 130 (FIG. 1). The RAM 802 may be the working memory for the processor 800, where data may be temporarily stored and from which instructions may be executed. Processor 800 couples to other devices within the controller 104 by way of the D/A converter 806 (e.g., the voltage generator 816), digital outputs 808 (e.g., the voltage generate 816), digital inputs 810 (i.e., push button switches 126, and the foot pedal assembly 130 (FIG. 1)), and other peripheral devices.

Voltage generator 816 generates selectable alternating current (AC) voltages that are applied to the electrodes of the wand 102. In the various embodiments, the voltage generator defines two terminals 824 and 826. In accordance with the various embodiments, the voltage generator generates an alternating current (AC) voltage across the terminals 824 and 826. In at least some embodiments the voltage generator 816 is electrically "floated" from the balance of the supply power in the controller 104, and thus the voltage on terminals 824, 826, when measured with respect to the earth ground or common (e.g., common 828) within the controller 104, may or may not show a voltage difference even when the voltage generator 816 is active.

The voltage generated and applied between the active terminal 624 and return terminal 626 by the voltage generator 616 is a RF signal that, in some embodiments, has a frequency of between about 5 kilo-Hertz (kHz) and 20 Mega-Hertz (MHz), in some cases being between about 30 kHz and 2.5 MHz, often between about 100 kHz and 200 kHz. In applications near the spine, a frequency of about 100 kHz appears most therapeutic. The RMS (root mean square) voltage generated by the voltage generator 816 may be in the range from about 5 Volts (V) to 1000 V, preferably being in the range from about 10 V to 500 V, often between about 100 V to 350 V depending on the active electrode size and the operating frequency. The peak-to-peak voltage generated by the voltage generator 816 for ablation or cutting in some embodiments is a square wave form in the range of 10 V to 2000 V and in some cases in the range of 100 V to 1800 V and in other cases in the range of about 28 V to 1200 V, often in the range of about 100 V to 320V peak-to-peak (again, depending on the electrode size and the operating frequency).

Still referring to the voltage generator 816, the voltage generator 816 delivers average power levels ranging from several milliwatts to hundreds of watts per electrode, depending on the voltage applied for the target tissue being treated, and/or the maximum allowed temperature selected for the wand 102. The voltage generator 816 is configured to enable a user to select the voltage level according to the specific requirements of a particular procedure. A description of one suitable voltage generator 816 can be found in commonly assigned U.S. Pat. Nos. 6,142,992 and 6,235,020, the complete disclosure of both patents are incorporated herein by reference for all purposes.

In some embodiments, the various operational modes of the voltage generator 816 may be controlled by way of digital-to-analog converter 806. That is, for example, the processor 800 may control the output voltage by providing a variable voltage to the voltage generator 816, where the voltage provided is proportional to the voltage generated by the voltage generator 816. In other embodiments, the processor 800 may communicate with the voltage generator by way of one or more digital output signals from the digital output 808 device, or by way of packet based communications using the communication device 812 (connection not specifically shown so as not to unduly complicate FIG. 8).

FIG. 8 also shows a simplified side view of the distal end 108 of the wand 102. As shown, illustrative electrode 202 of the wand 102 electrically couples to terminal 824 of the voltage generator 816 by way of the connector 120, and electrode 204 electrically couples to terminal 826 of the voltage generator 816.

As alluded to above, in certain electrosurgical procedures, such as discectomy procedures, it may not be possible to turn the wand 102 over when the distal end 108 is within a disc (i.e., the distance between vertebrae is smaller than the width of the wand); however, the surgical effect desired (e.g., ablation) may need to be applied to an upper portion of the disc, then a lower portion of the disc, and so on, as the distal end 108 of the wand moves within the disc. The various embodiments address the difficulties noted by a combination of an operational mode of the controller 104 and the relationship of illustrative electrodes 202 and 204. The operational mode of the controller 104 and relationship of the electrodes 202 and 204 will be discussed after a short digression into characteristics plasma creation and continuance.

In particular, in situations where plasma has yet to form but could form around any one of multiple electrodes, plasma tends to form in areas of highest current density. For example, as between two illustrative electrodes having the same exposed surface area of conductive material and same applied RMS voltage, during periods of time when RF energy is being applied across the electrodes but before plasma creation, the highest current density forms near the electrode closest to tissue of the patient. However, once plasma is formed a reduction in applied RF energy (to a point) will not necessarily extinguish the plasma, even in situations where another electrode would facilitate a higher current density if plasma creation was started anew.

In accordance with the various embodiments, a controller 104 is operated in a manner where plasma is created near a first electrode, and thus ablation takes place for a period of time, and then the plasma is extinguished (e.g., by a sufficient reduction in RF energy applied to the electrodes). Thereafter, the RF energy is again applied and thus plasma is created near whichever electrode produces the highest current density. Under the assumption that the ablation caused by the first plasma proximate to the first electrode removed tissue near the first electrode, when the RF energy is again applied in all likelihood the second electrode will then be closer to tissue than the first electrode, and thus the highest current density will be present near the second electrode and the plasma will be created near the second electrode.

More specifically, and in reference again to FIG. 8, in accordance with embodiments discussed above, the electrodes 202 and 204 have substantially the same exposed surface area of conductive material and also are symmetrically shaped. Voltage generator 816 initially applies RF energy across the terminals 824 and 826, and that RF energy is coupled to the electrodes 202 and 204. A plasma forms in the area of highest current density. For purposes of discussion, consider that the area of highest current density is initially near the electrode 202. Thus, plasma will initially form near the electrode 202 (meaning that electrode 202 becomes the active electrode), and electrode 204 acts a current return for the plasma (meaning that electrode 204 becomes the return electrode). After a predetermined period of time, the controller 104 reduces the RF energy output from the voltage generator 816 by an amount sufficient to extinguish the plasma, the reduction for a predetermined period of time, and then the voltage generator 816 again applies RF energy across the terminals 824 and 826. Now consider that because of ablation that took place near the electrode 202, when the RF energy is produced again the area of highest current density is near electrode 204. Thus, plasma will form near the electrode 204 (meaning that electrode 204 becomes the active electrode), and electrode 202 acts a current return for the plasma (meaning that electrode 202 becomes the return electrode). The cycle of producing energy, creating a plasma near an electrode, reducing energy sufficient to extinguish the plasma, and producing energy is repeated for extended periods of time. Thus, as the distal end 108 of the wand 102 is pushed through a disc, ablation takes places separately near each electrode, and in some cases (though not necessarily) alternately between the upper electrode 202 and lower electrode 204.

In the various embodiments the RF energy is applied for a predetermined period of time, in some cases between and including 50 milliseconds (ms) and 2000 ms, and in some cases 500 ms. As for reduction of RF energy sufficient to extinguish the plasma, in some cases the RF energy is reduced to zero (i.e., the voltage generator is turned off), but in other cases the RF energy remains non-zero, but is reduced an amount sufficient to extinguish the plasma where the amount of reduction is dependent upon the specific electrode configuration (e.g., in a particular electrode configuration a 50% reduction in RF energy may be sufficient). In some cases, the RF energy is reduced for at least 20 ms, and in some cases 50 ms. Before proceeding it should be understood that the RF energy applied across the terminals 824 and 826, and thus applied across the electrodes 202 and 204, is an AC voltage. By definition, and AC voltage swings from a positive value to a negative value, including a zero-crossing; however, changes in voltage associated with an applied AC waveform (e.g., sinusoidal, square) shall not be considered a "reduction" in voltage for purposes of this disclosure and claims.

In accordance with at least some embodiments, the cycle of producing RF energy at a particular level, reducing the RF energy, and then producing the RF energy again is an automatic function of the controller 104. Stated otherwise, once selected as the operational mode (e.g., by actuation of a foot pedal device, by interaction with switches 126, or possibly by wand specific inputs from the wand connector) when operated in the mode described the surgeon need not take action during the procedure to facilitate the cycle; rather, the cycle takes place during periods of time when the controller 104 is commanded to produce RF energy. Consider, as a specific example, a surgeon performing a discectomy. The surgeon selects an operational mode (e.g., by the switches 126), then commands production of RF energy by stepping on and holding down foot pedal device 132. In other words, stepping on and holding the foot pedal device indicates a command to produce energy. While the foot pedal device is depressed (i.e., while the controller 104 is commanded to produce RF energy), the RF energy IS produced, reduced, and re-produced in the cycle described above many times per second. Stated otherwise, in spite of the fact the surgeon has commanded the controller 104 to produce energy, the controller 104 may nevertheless reduce the RF energy, and in some cases turn the RF energy off, to extinguish the plasma as described above. Stated otherwise yet further still, forming the plasma proximate the first electrode, and then forming the plasma proximate the second electrode, is in the absence of a command provided to the electrosurgical controller to change an active electrode.

Thus, an aspect of operation is enabling the plasma to form proximate to an electrode closest to the tissue to be treated. So as not to favor one electrode over another for purposes of plasma creation, the electrodes in accordance with at least some embodiments have equal or substantially equal exposed surface areas. Moreover, when plasma forms near one electrode that electrode becomes an active electrode, while the other electrode becomes a return electrode, and their roles reverse periodically. So that each electrode has a fair opportunity to be either the active or return electrode, in embodiments where the elongate shaft 106 is metallic the elongate shaft is not electrically grounded or electrically coupled to the generator 104. Stated otherwise, having an electrically grounded metallic elongate shaft may interfere with the plasma creation aspects.

The cycle of production of energy, reduction of energy, and re-production of energy may be implemented in many forms. For example, in some cases when a particular operational mode is selected for the controller 104, the processor 800 executes a program that periodically commands the voltage generator 816 to reduce the RF energy (again, the reduction in some cases to zero) in order to extinguish the plasma. In yet still other embodiments, the voltage generator 816 itself may implement circuitry to perform the cycle as discussed.

Returning briefly to FIG. 3B, FIG. 3B shows the "slicing" effect of the illustrative wire loop electrodes. In relation to the cyclic plasma creation, it can now be pointed out that, as a wand 102 is pushed through a target tissue like a disc between vertebrae, the "slicing" action may take place with respect to the upper electrode 202, then because of the substantially similarity of the exposed surface areas of the conductive material, and the ablated tissue near the upper electrode, when plasma is created anew that plasma will in all likelihood be created near the lower electrode 204 (though the tissue near the lower electrode 204 is not shown in FIG. 3B).

Figure 9:
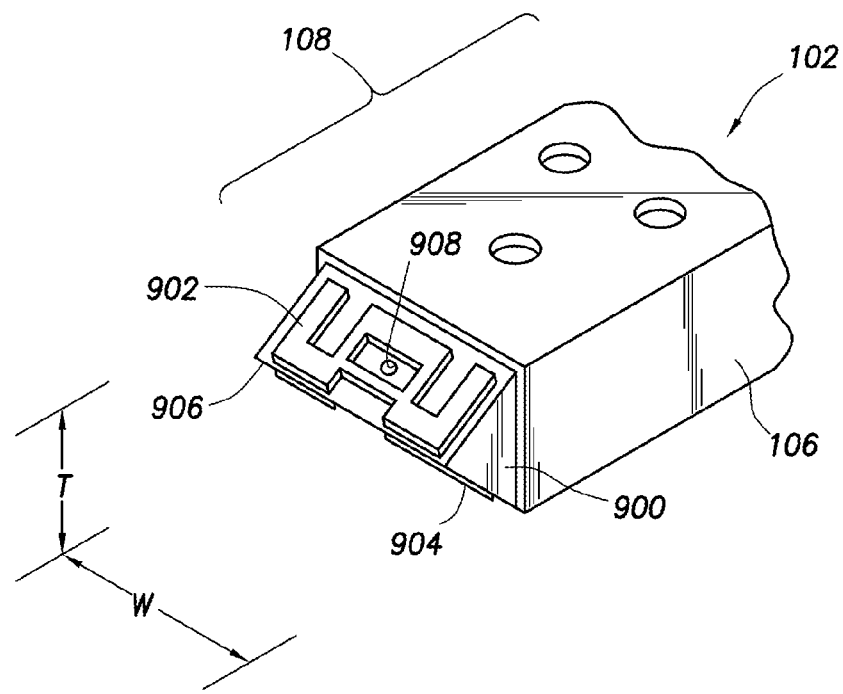
FIG. 9 shows a perspective view of a portion of a wand in accordance with at least some embodiments.

However, while there may be benefits to the "slicing" action of the wire electrodes of FIGS. 2, 3A and 3B, such "slicing" action is not required, and target tissue to be removed may be more fully ablated. FIG. 9 shows the distal end of a wand 102 in accordance with yet still other embodiments. In particular, the distal end 108 defines a width (labeled W in the figure) and a thickness (labeled T in the figure). In some embodiments the elongate shaft 106 is made of a metallic material (e.g., Grade TP304 stainless steel hypodermic tubing). In other embodiments, the elongate shaft may be constructed of other suitable materials, such as inorganic insulating materials. For the reasons discussed with respect to the wand 102 embodiments of FIGS. 3A and 3B, in at least some embodiments the metallic material of the elongate shaft 106 is not electrically grounded or electrically coupled to the generator of the controller 104. The elongate shaft 106 may define a circular cross-section at the handle or proximal end 110 (not shown in FIG. 9), and the distal end 108 may be flattened to define rectangular cross-section. In other embodiments, the flattened portion may define a semi-circular cross section. For wands intended for use in spinal procedures, the width W may be a centimeter or less, and in some cases a 5 millimeters. Likewise, for wands intended use in spinal procedures, the thickness T is 4 millimeters or less, and in some cases 3 millimeters. Other dimensions, particularly larger dimensions, may be equivalently used when the surgical procedure allows.

In embodiments where the elongate shaft is metallic, the distal end 108 may further comprise a non-conductive spacer 900 coupled to the elongate shaft 106. In some cases the spacer 200 is ceramic, but other non-conductive materials resistant to degradation when exposed to plasma may be equivalently used. The spacer 900 supports electrodes of conductive material, with illustrative electrodes labeled 902 and 904 in FIG. 9. In accordance with at least some embodiments, the upper electrode 202 is disposed above a plane that bisects the thickness, and with the lower electrode 204 disposed below the plane that bisects the thickness. Each electrode 902 and 904 defines an exposed surface area of conductive material, and in accordance with at least some embodiments the exposed surface area as between the upper electrode 902 and the lower electrode 904 is the same or substantially the same. In the particular embodiment of FIG. 9, each electrode 902 and 904 is a metallic fixture set at an angle such that the upper electrode 902 slopes towards the distal end 906 of the spacer 900. The exposed surface area for a particular wand depends, at least in part, on the parasitic stimulation of muscle and/or nerves that can be tolerated by the particular medical procedure. Greater parasitic stimulation is present with greater exposed surface area of the electrodes, and less parasitic stimulation is present with less exposed surface area. In embodiments as in FIG. 9, in some cases the exposed surface area of each electrode may range from 0.005 square inches to 0.030 square inches, and in a particular embodiment 0.020 square inches.

In accordance with at least some embodiments, not only do the electrodes define substantially the same exposed surface area as between the upper and lower electrodes, but also the shape as between the upper and lower electrodes is symmetric. In particular, the upper electrode 902 defines a particular shape, and likewise the lower electrode defines a particular shape. The shapes defined by the electrodes 902 and 904 are symmetric about a plane that bisects the thickness T. More particularly still, in some embodiments the electrodes 202 and 204 are mirror images of each other reflected about a plane that bisects the thickness. In other embodiments, the shape of the electrodes may be non-symmetrical, even if the exposed surface areas are substantially the same.

In some embodiments saline is delivered to the distal end 108 of wand, possibly to aid in plasma creation. FIG. 9 illustrates a discharge aperture 908 on the distal end 108 within electrode 902. A similar discharge aperture is present with respect to electrode 904, but is not visible in the view of FIG. 9. While two discharge apertures are contemplated in FIG. 9, a single discharge aperture may be used (e.g., disposed through the distal end 906 of the spacer), and likewise multiple (even non-symmetric) discharge apertures associated with each electrode 902 and 904. The discharge apertures fluidly couple to the flexible tubular member 116 (FIG. 1) by way of a fluid conduit within the wand 102. Thus, saline or other fluid may be pumped into the flexible tubular member 116 (FIG. 1) and discharge through the discharge apertures. In yet still further embodiments, aspiration is provided at the distal end 108 of the wand 102. FIG. 9 illustrates aspiration apertures 220, 222 and 224, which operate similarly to those discussed with respect to FIGS. 3A and 3B.

The embodiments of FIG. 9 operate similarly to the wire loop embodiments in the sense that each electrode 902 and 904 are coupled to the terminals 824 and 826, respectively, and that plasma will be created near the electrode where current density is the greatest. Moreover, the cycling RF energy may extinguish the plasma near one electrode, and enable plasma creation near the other electrode. Unlike the embodiments of FIGS. 3A and 3B, however, the electrodes of FIG. 9 do not necessarily "slice" tissue; rather, the electrodes 902 and 904 of FIG. 9 may be used in situation where the desire is to ablate substantially all tissue that is to be removed.

Figure 10:
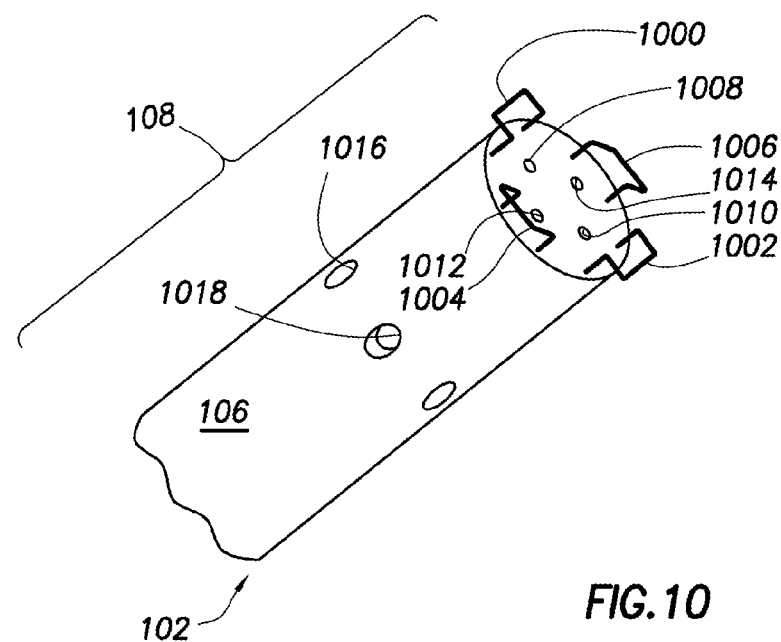
FIG. 10 shows a perspective view of a portion of a wand in accordance with at least some embodiments.

While the various embodiments discussed to this point have all been in relation to wands 102 having two electrodes, in yet still other embodiments more electrodes may be used. For example, FIG. 10 illustrates alternative embodiments of the distal end 108 of a wand 102 with four electrodes. In particular, FIG. 10 illustrates the elongate shaft 106 defining a circular cross-section, even at the distal end. Moreover, the wand 102 has four electrodes 1000, 1002, 1004 and 1006, with each electrodes illustrated as a wire loop electrode (though wire loops are not required). In these embodiments, the electrodes couple in pairs to the terminals of the voltage generator 816 of the controller 104. For example, electrodes 1000 and 1002 may couple to the terminal 824 (FIG. 8), and electrodes 1004 and 1006 may couple to the terminal 826. Thus, plasma may be created proximate to the pair of electrodes that create the highest current density (to become the active electrodes), and the remaining pair will acts a return electrodes, with the designation as active or return changing intermittently as the plasma is re-formed responsive to the generator operation as discussed above.

Moreover, FIG. 10 also illustrates more than two discharge apertures may be used, such as the illustrative four discharge apertures 1008, 1010, 1012 and 1014. Finally, FIG. 10 illustrates aspiration apertures 1016 and 1018, which operate similarly to the aspiration apertures discussed with respect to the other embodiments.

Figure 11:
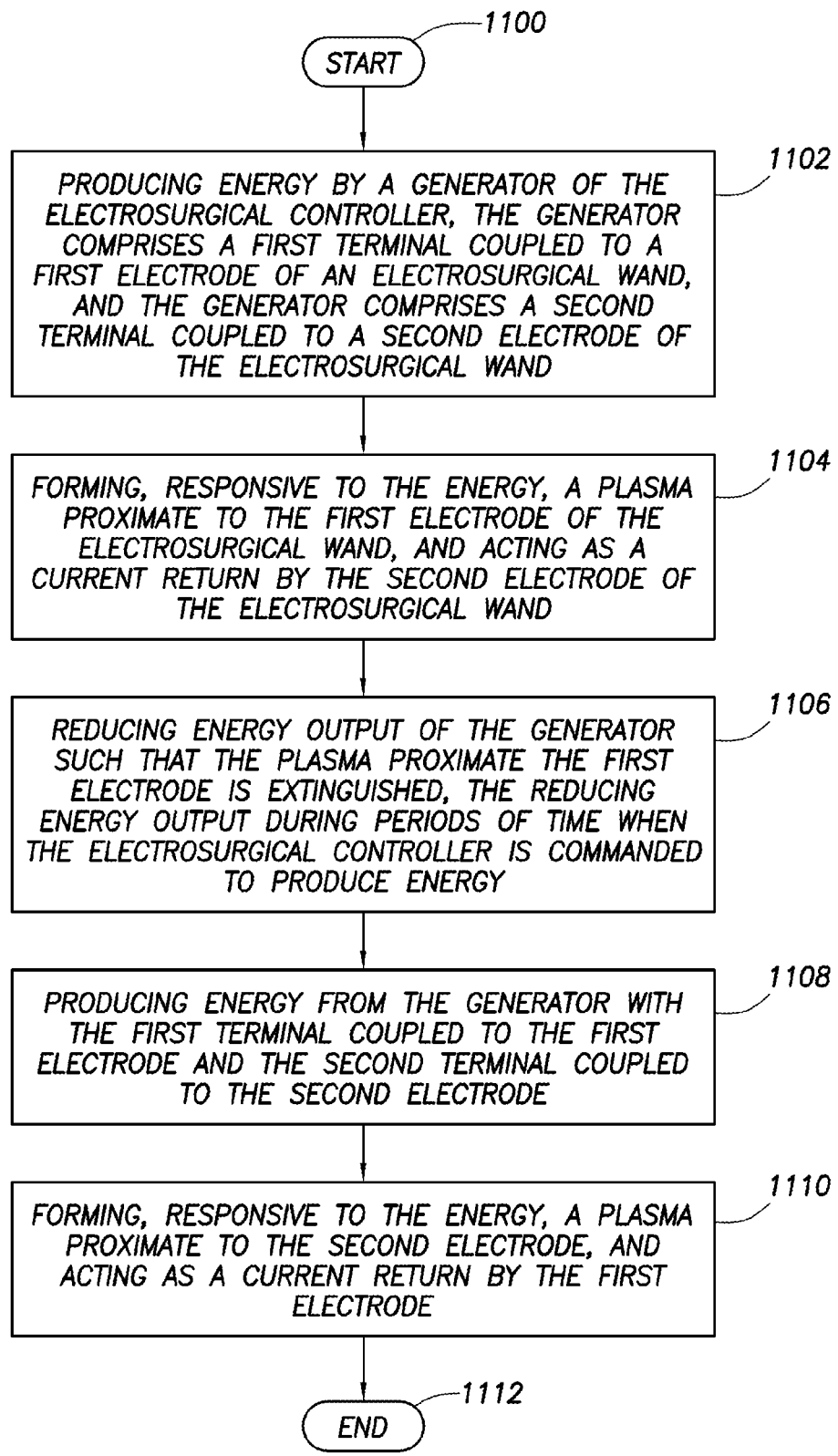
FIG. 11 shows a method in accordance with at least some embodiments.

FIG. 11 shows a method in accordance with at least some embodiments. In particular, the method starts (block 1100) and comprises: producing energy by a generator of the electrosurgical controller, the generator comprises a first terminal coupled to a first electrode of an electrosurgical wand, and the generator comprises a second terminal coupled to a second electrode of the electrosurgical wand (block 1102); forming, responsive to the energy, a plasma proximate to the first electrode of the electrosurgical wand, and acting as a current return by the second electrode of the electrosurgical wand (block 1104); reducing energy output of the generator such that the plasma proximate the first electrode is extinguished, the reducing energy output during periods of time when the electrosurgical controller is commanded to produce energy (block 1106); producing energy from the generator with the first terminal coupled to the first electrode and the second terminal coupled to the second electrode (block 1108); and forming, responsive to the energy, a plasma proximate to the second electrode, and acting as a current return by the first electrode (block 1110). And thereafter the method ends (block 1112).

FIG. 12 shows another method in accordance with at least some embodiments. In particular, the method starts (block 1200) and proceeds to treating a disc between vertebrae of a spine (block 1202). The treating the disc is by: inserting an electrosurgical wand to abut a portion of the disc (block 1204); commanding an electrosurgical controller to supply radio frequency energy to electrosurgical wand (block 1206); producing energy by a generator of the electrosurgical controller, the generator comprises a first terminal coupled to a first electrode of the electrosurgical wand, and the generator comprises a second terminal coupled to a second electrode of the electrosurgical wand (block 1208); ablating a portion of the disc by a plasma proximate to the first electrode of the electrosurgical wand, and acting as a current return by the second electrode of the electrosurgical wand (block 1210); reducing energy output of the generator such that the plasma proximate the first electrode is extinguished, the reducing energy output during periods of time when the electrosurgical controller is commanded to produce energy (block 1212); producing energy from the generator with the first terminal coupled to the first electrode and the second terminal coupled to the second electrode (block 1214); and ablating a portion of the disc by a plasma proximate to the second electrode, and acting as a current return by the first electrode (block 1216). Thereafter, the method ends (block 1218).

The above discussion is meant to be illustrative of the principles and various embodiments of the present invention. Numerous variations and modifications possible. For example, while in some cases electrodes were designated as upper electrodes and lower electrodes, such a designation was for purposes of discussion, and shall not be read to require any relationship to gravity during surgical procedures. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical wand comprising:
    an elongate shaft that defines a proximal end and a distal end, the elongate shaft at the distal end defines a width and a thickness;
    a connector comprising a first and second electrical pin;
    a first electrode of conductive material disposed on a first angled planar surface of the distal end of the elongate shaft, the first electrode defines a first exposed surface area, the first electrode electrically coupled to the first electrical pin, and the first electrode disposed above a plane that bisects the thickness of the distal end of the elongate shaft;
    a second electrode of conductive material disposed on a second angled planar surface of the distal end of the elongate shaft, the second electrode defines a second exposed surface area substantially the same as the first exposed surface area, the second electrode electrically coupled to the second electrical pin, and the second electrode disposed below the plane that bisects the thickness of the distal end of the elongate shaft, and wherein the first and second angled planar surface are oriented at opposing angles relative to the plane that bisects the thickness such that the angled planar surfaces slope towards each other as they extend distally;
    a first fluid conduit within the elongate shaft, the first fluid conduit defines a first discharge aperture on the distal end of the elongate shaft;
    a second fluid conduit within the elongate shaft, the second fluid conduit defines a first aspiration aperture on the distal end of the elongate shaft.

2. The electrosurgical wand of claim 1 wherein the first electrode defines a shape, the second electrode defines a shape, and wherein the shapes defined are symmetric about the plane that bisects the thickness of the distal end.

3. The electrosurgical wand of claim 1 wherein when fluid flows through the first conduit and out the first discharge aperture, the fluid is directed out of the first discharge aperture and through the first electrode.

4. The electrosurgical wand of claim 3 further comprising a second discharge aperture on the distal end of the elongate shaft, the second discharge aperture fluidly coupled to the first fluid conduit, and when fluid flows through the first conduit and out the second discharge aperture, the fluid is directed out through the second electrode.

5. The electrosurgical wand of claim 3, wherein the fluid is directed approximately along the plane that bisects the thickness of the distal end.

6. The electrosurgical wand of claim 1 wherein the first aspiration aperture is within 5 (five) centimeters of the first and second electrodes.

7. The electrosurgical wand of claim 1 wherein a portion of the elongate shaft is an electrically conductive material, and the electrically conductive material is electrically insulated from the first and second electrical pins of the connector.

8. The electrosurgical wand of claim 1 wherein the distal end of the elongate shaft defines a wand tip axis, and a medial portion of the elongate shaft defines a medial axis, that is oriented at an angle that is non-zero relative to the wand tip axis.

9. The electrosurgical wand of claim 1, wherein the first electrode defines a first shape having at least five sides, the second electrode defines a second shape, and wherein the first and second shapes are a mirror image of each other about the plane that bisects the thickness of the distal end.

10. The electrosurgical wand of claim 1 wherein the first and second electrical pins are in electrical communication with a generator of an electrosurgical controller, and wherein when energy is applied to the first and second electrical pins, the electrodes are configured such that a plasma is formed at either of the first or second electrodes sufficient to volumetrically remove a target tissue.

11. The electrosurgical wand of claim 1 wherein the first and second angled planar surfaces are oriented equal and opposite relative to the plane that bisects the thickness of the distal end of the elongate shaft.

12. The electrosurgical wand of claim 1 wherein the first and second electrical pins are in electrical communication with a generator of an electrosurgical controller, and wherein when energy is applied to the first and second electrical pins, the first electrode is configured so that a plasma is formed at the first electrode, causing the second electrode to act as a return electrode.

\* \* \* \* \*